(12) United States Patent
Ulmer

(10) Patent No.: US 10,709,820 B2
(45) Date of Patent: Jul. 14, 2020

(54) METHOD FOR PRODUCING A STORABLE MOLDED BODY MADE OF BACTERIAL CELLULOSE

(71) Applicant: BIOTRONIK AG, Buelach (CH)

(72) Inventor: Jens Ulmer, Kuesnacht (CH)

(73) Assignee: BIOTRONIK AG, Buelach (CH)

( * ) Notice: Subject to any disclaimer, the term of this patent is extended or adjusted under 35 U.S.C. 154(b) by 0 days.

(21) Appl. No.: 15/523,614

(22) PCT Filed: Nov. 24, 2015

(86) PCT No.: PCT/EP2015/077463
§ 371 (c)(1),
(2) Date: May 1, 2017

(87) PCT Pub. No.: WO2016/083351
PCT Pub. Date: Jun. 2, 2016

(65) Prior Publication Data
US 2017/0312398 A1 Nov. 2, 2017

Related U.S. Application Data

(60) Provisional application No. 62/083,332, filed on Nov. 24, 2014.

(51) Int. Cl.
| | | |
|---|---|---|
| A61L 31/04 | (2006.01) | |
| A61L 27/20 | (2006.01) | |
| A61L 29/04 | (2006.01) | |
| A61F 2/24 | (2006.01) | |
| A61B 17/12 | (2006.01) | |

(Continued)

(52) U.S. Cl.
CPC ...... *A61L 31/042* (2013.01); *A61B 17/12122* (2013.01); *A61F 2/062* (2013.01);
(Continued)

(58) Field of Classification Search
CPC .... C08L 1/02; C08L 69/00; C08L 1/08; C08L 1/12; C08L 23/16; C08L 2666/02; C08L 71/02; C08L 29/04; C08L 21/00; C08L 2205/16; C08L 39/06; C08L 33/08; C08L 7/02; C08L 53/00; C08L 2205/04; C08K 7/02; C08K 5/19; C08K 2201/004; C08K 2201/014; C08B 3/06; C08B 3/12; C08B 15/05; C08G 63/672; C08G 77/388; C08J 2367/06; C08J 5/045; C08J 5/06; C08J 2321/02; C08J 2433/02; C08J 2433/06; C08J 7/0427; C08J 7/18; Y10T 428/3179; Y10T 428/31975; Y10T 428/2922; Y10T 428/298; A61B 17/12122; A61B 2017/00526; A61B 17/00526; A61B 17/205; A61F 2007/0098; A61F 2007/038; A61F 2210/0061; A61F 2220/0016; A61F 2240/001; A61F 2250/0014; A61F 2250/0069; A61F 2/062; A61F 2/07; A61F 2/08; A61F 2/2409; A61F 2/2415; A61F 2/2418; A61F 7/034; A61L 2300/23; A61L 2300/41; A61L 2430/10; A61L 2430/20; A61L 24/0015; A61L 24/08; A61L 27/54; A61L 29/043; A61L 29/16; A61L 31/16; A61L 27/34; A61L 31/10; A61L 29/085; A61L 27/16; A61L 29/041; A61L 31/048; A61L 2400/10; A61L 2400/18; A61L 27/20; A61L 27/50; A61L 27/507; A61L 31/042; A61L 15/28; A61L 15/52; A61L 2300/114; A61L 2300/442; A61L 2400/06; A61L 2420/02; A61L 2420/06; A61L 2420/08; A61L 2430/16; A61L 27/14; A61L 27/225; A61L 27/3804; A61L 27/44; A61L 31/049; A61L 31/14; A61N 1/362;

(Continued)

(56) References Cited

U.S. PATENT DOCUMENTS

| | | | |
|---|---|---|---|
| 4,588,400 | A | 5/1986 | Ring et al. |
| 4,655,758 | A | 4/1987 | Ring et al. |

(Continued)

FOREIGN PATENT DOCUMENTS

| | | | |
|---|---|---|---|
| CN | 102690773 | * | 9/2012 |
| DE | 4027479 | A1 | 1/1992 |
| EP | 1267753 | B1 | 10/2005 |
| EP | 1660670 | A | 5/2006 |
| EP | 0866678 | B1 | 9/2007 |
| EP | 1569578 | B1 | 11/2007 |
| EP | 2380526 | A2 | 10/2011 |
| EP | 2484406 | A1 | 8/2012 |

OTHER PUBLICATIONS

Galvez, Joelle, et al., "Notification of Transmittal of the International Search Report and the Written Opinion of the International Searching Authority, or the Declaration", Patent Cooperation Treaty Application No. PCT/EP2015/077463, European Patent Office as International Searching Authority, International Search Completed Feb. 16, 2016, International Search Report dated Feb. 23, 2016, (12 pages).

*Primary Examiner* — Deborah K Ware
(74) *Attorney, Agent, or Firm* — Greer, Burns & Crain, Ltd; Steven P. Fallon

(57) ABSTRACT

A method for producing a storable molded body made of bacterial cellulose and a molded body produced according to the method. A preferred method includes providing a molded body made of bacterial cellulose. Optionally, mechanically pressing the entire molded body or parts of the molded body at temperatures in the range of 10° C. to 100° C. and pressures in the range of 0.01 to 1 MPa for a pressing time of 10-200 min. Treating the molded body with a solution of 20% by weight to 50% by weight of glycerol and 50% by weight to 80% by weight of a C1-C3-alcohol/water mixture. Drying the treated molded body.

24 Claims, 6 Drawing Sheets

(51) Int. Cl.
| | |
|---|---|
| A61F 2/06 | (2013.01) |
| A61F 2/07 | (2013.01) |
| A61F 2/08 | (2006.01) |
| A61L 24/00 | (2006.01) |
| A61L 24/08 | (2006.01) |
| A61L 27/50 | (2006.01) |
| A61L 27/54 | (2006.01) |
| A61L 29/16 | (2006.01) |
| A61L 31/10 | (2006.01) |
| A61L 31/16 | (2006.01) |
| A61N 1/362 | (2006.01) |
| A61N 1/375 | (2006.01) |
| A61N 1/39 | (2006.01) |
| B30B 11/00 | (2006.01) |
| C12P 19/04 | (2006.01) |
| D21C 5/00 | (2006.01) |
| A61L 31/14 | (2006.01) |
| A61L 27/36 | (2006.01) |
| A61L 27/56 | (2006.01) |
| A61F 2/915 | (2013.01) |
| A61L 27/58 | (2006.01) |
| A61B 17/00 | (2006.01) |

(52) U.S. Cl.
CPC .................. *A61F 2/07* (2013.01); *A61F 2/08* (2013.01); *A61F 2/24* (2013.01); *A61F 2/2409* (2013.01); *A61F 2/2415* (2013.01); *A61F 2/2418* (2013.01); *A61L 24/0015* (2013.01); *A61L 24/08* (2013.01); *A61L 27/20* (2013.01); *A61L 27/507* (2013.01); *A61L 27/54* (2013.01); *A61L 29/043* (2013.01); *A61L 29/16* (2013.01); *A61L 31/10* (2013.01); *A61L 31/16* (2013.01); *A61N 1/362* (2013.01); *A61N 1/3754* (2013.01); *A61N 1/3956* (2013.01); *B30B 11/005* (2013.01); *C12P 19/04* (2013.01); *D21C 5/00* (2013.01); *A61B 2017/00526* (2013.01); *A61F 2/2412* (2013.01); *A61F 2/915* (2013.01); *A61F 2210/0004* (2013.01); *A61F 2210/0061* (2013.01); *A61F 2220/0016* (2013.01); *A61F 2220/0075* (2013.01); *A61F 2230/0058* (2013.01); *A61F 2240/001* (2013.01); *A61F 2250/0014* (2013.01); *A61F 2250/0023* (2013.01); *A61F 2250/0036* (2013.01); *A61F 2250/0051* (2013.01); *A61F 2250/0069* (2013.01); *A61L 27/3691* (2013.01); *A61L 27/56* (2013.01); *A61L 27/58* (2013.01); *A61L 31/146* (2013.01); *A61L 2300/23* (2013.01); *A61L 2300/41* (2013.01); *A61L 2400/18* (2013.01); *A61L 2430/10* (2013.01); *A61L 2430/20* (2013.01)

(58) Field of Classification Search
CPC .. A61N 1/3754; A61N 1/3956; B30B 11/005; B82Y 40/00; C09K 5/18; C12P 19/04; C12P 13/002; C12P 13/04; C12P 41/006; C12P 7/42; C12P 7/62; D06M 13/46; D06M 2101/08; D06M 23/10; D21C 5/00; F16G 1/08; F16G 5/06; F16G 5/20; F24V 30/00; A61K 38/00; A61K 51/0453; A61K 2300/00; A61K 31/00; A61K 31/74; A61K 31/787; A61K 39/00; A61K 47/10; A61K 47/34; A61K 47/36; A61K 8/84; A61K 9/0024; A61K 47/14; A61K 47/24; A61K 47/32; A61K 47/38; A61K 8/046; A61K 8/86; A61K 9/0014; A61K 9/0021; A61K 9/0051; A61K 9/06; A61K 9/1647; A61K 2800/31; A61K 31/155; A61K 31/19; A61K 31/33; A61K 31/337; A61K 31/37; A61K 31/404; A61K 31/496; A61K 31/573; A61K 31/7036; A61K 31/727; A61K 41/0028; A61K 47/02; A61K 47/40; A61K 47/44; A61K 8/31; A61K 8/342; A61K 8/345; A61K 8/361; A61K 8/4993; A61K 8/585; A61K 8/731; A61K 8/732; A61K 8/8147; A61K 8/891; A61K 9/0031; A61K 9/0034; A61K 9/0043; A61K 9/0046; A61K 9/0048; A61K 9/1075; A61K 9/12; A61K 9/122; A61K 9/124; A61K 9/1641; A61K 9/1658; A61K 9/5031; A61K 9/5052; C07B 59/002; C07B 2200/13; C07K 5/06078; C07K 5/06191; C07K 2317/55; C07K 16/00; C07D 407/06; C07D 209/18; C07D 401/06; C07D 409/06; C07D 401/12; C07D 401/14; C07D 403/06; C07D 413/06; C07D 413/14; C07D 417/06; C07D 417/14; C07D 498/04; C07D 209/22; C07D 209/30; C07D 209/42; C07D 403/14; C07D 209/32; C07H 13/04; C07H 15/12; C07H 15/04; C12M 47/12; C12N 9/0006; A01N 43/50; A01N 2300/00; A01N 43/56; A01N 43/653; A01N 47/24; A01N 25/02; A01N 25/10; A01N 31/02; A01N 37/04; A61Q 19/00; A61Q 17/00; A61Q 19/02; A61Q 19/08; A61Q 5/006; A61Q 7/00; C08F 220/20; C08F 220/06; C08F 220/28; C07C 67/31; C07C 69/734; C07C 59/58; A61M 2037/003; A61M 2037/0046; A61M 2037/0053; A61M 2205/36; A61M 2205/3606; A61M 2205/3633; A61M 2205/3653; A61M 2207/00; A61M 37/0076; A61M 5/3015; A61M 5/3298; C09D 133/06; C09D 133/066; C11D 11/0029; C11D 3/044; C11D 3/10; C11D 3/2086; C11D 7/06; C11D 7/12; C11D 7/265; C04B 24/2641; C12Y 304/21068; C12Y 304/24069; G02B 1/043; G02C 7/04

See application file for complete search history.

(56) References Cited

U.S. PATENT DOCUMENTS

| | | | | |
|---|---|---|---|---|
| 6,468,668 | B1* | 10/2002 | Minami | .................. C08B 3/12 |
| | | | | 424/488 |
| 7,454,251 | B2 | 11/2008 | Rezai et al. | |
| 8,158,427 | B2* | 4/2012 | Wilson | .................. C12M 23/08 |
| | | | | 435/401 |
| 8,252,051 | B2 | 8/2012 | Chau et al. | |
| 2002/0107223 | A1 | 8/2002 | Oster et al. | |
| 2008/0177021 | A1* | 7/2008 | Berlin | .................. A61L 27/18 |
| | | | | 528/10 |
| 2010/0159046 | A1 | 6/2010 | Harris et al. | |
| 2011/0208298 | A1 | 8/2011 | Tuval et al. | |
| 2012/0053677 | A1 | 3/2012 | Ferrari et al. | |
| 2012/0171354 | A1* | 7/2012 | O'Neill | .................. A61L 27/34 |
| | | | | 427/2.25 |
| 2013/0018458 | A1 | 1/2013 | Ziv et al. | |
| 2013/0197622 | A1 | 8/2013 | Mitra et al. | |

* cited by examiner

METHOD FOR PRODUCING A STORABLE MOLDED BODY MADE OF BACTERIAL CELLULOSE

TECHNICAL FIELD

The invention relates to a method for producing a storable molded body made of bacterial cellulose and a molded body produced according to the method. The invention also concerns materials for medical implants and medical implants.

BACKGROUND

In the field of modern medical technology, highly diverse types of materials are used as implant materials. The substance characteristics of these materials that are decisive for the particular field of application are, in particular, the biocompatibility and mechanical properties of these materials. Bacterial cellulose is a promising biocompatible material.

Bacterial cellulose is an extracellular metabolic product formed by microorganisms and has properties that are comparable to those of plant-based cellulose. The purity is significantly higher, however, since there are no foreign polymers or other inclusions contained therein.

The supramolecular structure thereof gives bacterial cellulose a highly hydrophilic character, high absorbing capacity and mechanical strength. Of all cellulose-forming microorganisms, the gram-negative aerobic species *Gluconacetobacter xylinus*, formerly also known as *Acetobacter xylinum* is of particular significance.

Disadvantageously, however, the mere dehydration and renewed hydration of the cellulose results in a distinct loss of volume. Moreover, conventionally dehydrated cellulose is very brittle. As a result, conventional implants that comprise bacterial cellulose in entirety or in parts cannot be stored.

SUMMARY

One or more of the aforementioned problems associated with the prior art can be eliminated or at least ameliorated by methods of the invention, for producing a storable molded body made of bacterial cellulose. A preferred method includes the steps of:
i) providing a molded body made of bacterial cellulose;
ii) optionally, mechanically pressing the entire molded body or parts of the molded body at temperatures in the range of 10° C. to 100° C. and pressures in the range of 0.0005 to 1.5 MPa, preferably 0.01 to 1 MPa for a pressing time of 10-200 min;
iii) treating the molded body with a solution of 20% by weight to 50% by weight of glycerol and 50% by weight to 80% by weight of a C1-C3-alcohol/water mixture; and
iv) drying the treated molded body.

The invention also provides a storable molded body made of treated bacterial cellulose, wherein the treated bacterial cellulose is dry and has a swelling capacity that is greater than untreated bacterial cellulose of the same type.

BRIEF DESCRIPTION OF THE DRAWINGS

The present invention is explained in greater detail in the following with reference to drawings and embodiments. In the drawings.

DETAILED DESCRIPTION OF THE PREFERRED EMBODIMENTS

Figure 1:
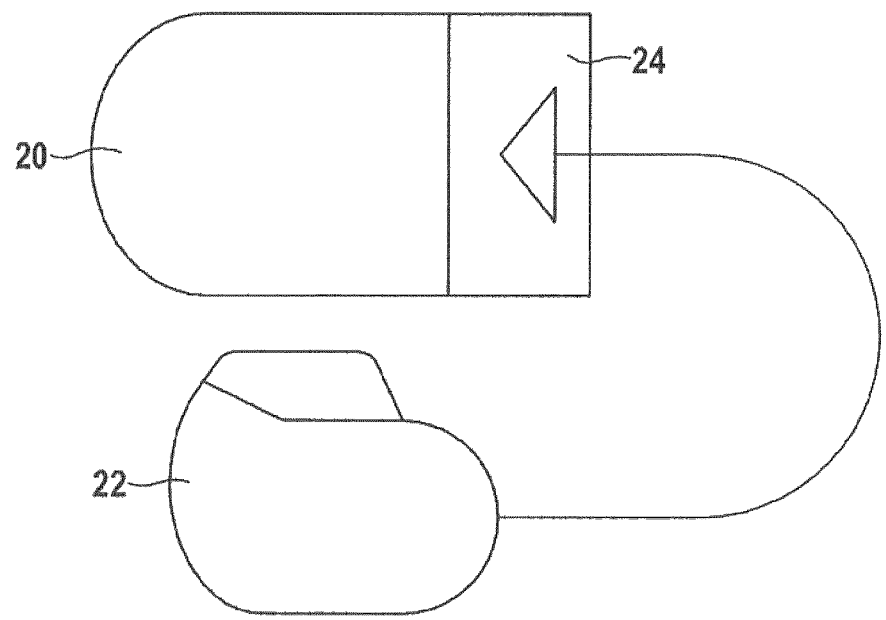
FIG. 1 shows a first embodiment of the molded body according to the invention, in the form of an implant shell for a pacemaker.

Preferred methods of the invention provide a molded body made of bacterial cellulose, in particular bacterial cellulose from *Gluconacetobacter xylinus*, that has been treated according to the above-described drying process, that is now storable, since the bacterial cellulose is no longer brittle, due to the drying, as is the case with conventional drying processes. The cellulose can now be processed and stored in the dry state without losing the positive characteristics of the material. It was shown, for example, that the anti-inflammatory properties and good biocompatibility are retained, as is the high mechanical strength as well as the swelling capacity of the material. The swelling capacity can be set to different levels by applying different pressure levels to different parts of the molded body, as well as by pressing different parts of the molded body.

The bacterial cellulose is initially provided in a form that is suitable for the subsequent application. For example, layers of bacterial cellulose are separated out of nutritive solutions, which contain glucose and were inoculated with *Gluconacetobacter xylinus*, in a manner known per se, and are then air-dried. It is also conceivable that a covering of high-purity cellulose fibers is allowed to grow directly on a carrier material, for example the metallic base body of a stent.

A newly developed culture vessel has made it possible to produce layers of bacterial cellulose having different material thicknesses. To this end, the culture vessel comprises a gas-permeable silicone layer, the thickness of which varies, and which is in contact with the culture solution to be accommodated in the culture vessel. In regions of reduced thickness of the silicone layer, more air diffuses to the boundary layer between the culture solution and the silicone layer, with the result that the aerobic bacterial growth is increased in this region, and therefore cellulose deposits here to an increasing extent. Layers of bacterial cellulose can be produced in this manner, for example, that have a layer thickness that varies in the range of 2 to 10 mm. Consequently, it is possible to provide suitable implantation material with a higher thickness than natural material of human or animal origin suitable for the preferred applications as prosthetic material for heart valves.

Additional preparatory measures may be required to provide the required molded body of bacterial cellulose, such as purification, pressing, pre-drying, assembly, and cutting the material into the required shape and size.

Bacterial cellulose which is to be used for medical implants calls for a high standard in terms of purity, particularly related to pyrogenic molecules. The layers of bacterial cellulose can contain residual bacteria, which may not be efficiently removed by conventional methods such as washing in aqueous alkaline solution (DE 40 27 479 A1, U.S. Pat. No. 4,588,400 A) and use of detergents, such as sodium dodecyl sulfate (SDS, EP 1 660 670 A). Therefore, in a preferred embodiment the first step i) of the inventive method comprises the sub-steps of:
  a) transferring the body of bacterial cellulose into an aqueous solution of 1-10% by weight of at least one surfactant and 0.4-4% by weight of at least one base,
  b) treating the body of bacterial cellulose by means of microwaves at a temperature of at least 80° C., but less than 100° C., for 30-60 min,
  c) washing the body of bacterial cellulose in a solution of aqueous weak acid in combination with application of microwaves, and rinsing with water.

In the sub-steps a) and b) any bacteria present yet in the cellulose material are killed by the alkaline surfactant solution and quickly lysed by the microwave radiation. Consequently the bacteria are efficiently killed and destroyed. The washing sub-step c) facilitates a neutralization of the bacterial cellulose as well as a quick removal of bacterial particles, including any endotoxins and/or pyrogenic remnants. Furthermore the inventive method is faster and works with milder detergents than conventional methods of cleaning bacterial cellulose. Consequently the embodiment is advantageous because they allow a particular efficient production of bacterial cellulose which is free of pyrogens.

The concentration of the surfactant is preferably 1-10% by weight, more preferred 2-8% by weight, more preferred 3-6% by weight, and particularly preferred 4% by weight. The concentration of the at least one base is preferably 0.4-4% by weight, more preferred 0.6-3% by weight, more preferred 0.8-2% by weight, and particularly preferred 1% by weight.

Suitable bases can be selected from the group comprising or consisting of alkali and earth alkali hydroxide such as sodium hydroxide, potassium hydroxide, alkali and earth alkali carbonates, alkali and earth alkali hydrogencarbonate, ammonia and triethyl amine.

Anionic, nonionic and zwitterionic surfactants can be used in the invention. It is also possible to use a combination of surfactants. Anionic surfactants to be used comprise sodium cholate, sodium deoxycholate, sodium glycocholate, sodium taurodeoxycholate, taurocholic acid, N-lauroylsarcosine, and sodium dodecyl sulfate. Nonionic surfactants to be used comprise N,N-Bis(3-(D-gluconamido)-propyl)deoxycholamide, digitoin, saponins, polidocanol, Dodecyldimethyl-phosphine oxide, Dimethyldecylphosphine oxide, Octyl-b-glucopyranoside, Decyl-b-maltopyranoside, decyl-b-1-thiomaltopyranoside, octyl-b-1-thioglucopyranoside, undecyl-b-maltoside, n-dodecyl-b-maltoside, 6-cyclohexylhexyl-b-maltoside, Triton-X-100, Triton-X-140, Tween 20, Tween 80, NP-40, Brij-35, Brij-58, octyl glucoside, octyl thioglucoside, and surfactin. Zwitterionic surfactants to be used comprise ASB-14, ASB-16, C7BzO, CHAPS, CHAPSO, EMPGEN BB.

The temperature in sub-step b) shall not rise above 100° C. because the solution is not supposed to boil, which could lead to the evolution of gas causing damage to the bacterial cellulose. Within the preferred temperature window of 80 to 100° C., it is more preferred if the temperature is between 85 and 95° C., and yet more preferred if the temperature is around 90° C. The energy level and timing of the microwave radiation is set to a point which allows controlling the temperature in said temperature window.

The washing with weak acid such as acetic acid, oxalic acid or phosphoric acid, in sub-step c) serves for neutralization of the bacterial cellulose after the treatment with the alkaline solution in step b). Alternatively to weak acids such as acetic acid, diluted hydrochloric acid, nitric acid or sulfuric acid and the like can be used for washing. Instead of microwaves, vacuum filtration can be applied to support the washing in sub-step c).

It is particularly preferred if after sub-step b) an additional sub-step is to be performed:
  b') incubating the body of bacterial cellulose in an enzymatic solution of at least one lytic enzyme at about 37° C. for at least 15 min.

The enzymatic treatment step b' is advantageous because any residual bacteria yet present in the bacterial cellulose are lysed. The term lytic enzyme as used in this description refers to any enzyme which can be used for the lysis of bacteria and digestion of bacterial molecules.

Preferred enzymes are achromopeptidase, lysozyme, and amylase. It is possible to use one single enzyme in sub-step b'), as well as a combination of two enzymes, or a combination of three or more enzymes. The temperature and time of incubation can be varied depending on the enzymes. The enzymes are inactivated and removed by the washing and application of microwaves, or vacuum filtration, in sub-step c).

In the optional step ii) of the inventive method, the entire molded body or parts of the molded body are mechanically pressed at temperatures in the range of 10° C. to 100° C. and pressures in the range of 0.0005 to 1.5 MPa, preferably 0.01 to 1 MPa for a pressing time of 10-200 min.

A further preferred embodiment of the inventive process provides that in the second step ii) of the process the temperature is preferably in the range from 80° C. to 100° C. and the pressure is preferably in the range from 1.5 MPa to 2 MPa. In a different embodiment the pressure can be preferably in the range from 1.0 to 10 kPa and more preferably 1.5 kPa to 2 kPa at a temperature range of 80° C. to 100° C. The primary goal of the so-called hot pressing is to remove water present in the bacterial cellulose completely, or at least partially. The pressing is advantageous, because as a result of the pressing the swelling capacity of the cellulose is reduced and can be set to a desired level. Furthermore the mechanical stability of the cellulose is increased. However, the pressure shall not be too strong to avoid mechanical damage of the material or destruction in form of cutting or crushing.

In step iii) of the method according to the invention, the molded body that is made of bacterial cellulose and is required for the particular application is then washed with the C1-C3 alcohol/water mixture (for example, methanol, ethanol, 1-propanol and 2-propanol) and glycerol, in particular in a special isopropanol/water solution containing glycerol, or is incubated in the solution. The solution contains between 20% by weight and 50% by weight of glycerol. The remainder is formed by the C1-C3 alcohol/water mixture. The ratio of C1-C3 alcohol to water in the C1-C3 alcohol/water mixture is preferably between 90 to 10 and 70 to 30. Particularly preferred is a C1-C3 alcohol/water mixture of 80% by weight of C1-C3 alcohol, in particular isopropanol, and 20% by weight of water. The portion of water in the incubation solution of glycerol and C1-C3 alcohol/water mixture preferably does not exceed 20% by weight. The solution can contain further components, but is preferably limited to the aforementioned three components. The time period of the incubation in the solution is typically 0.5 to 24 h, and preferably 12 h.

Next, the molded body to be treated with the solution is dried. The drying can be carried out as air-drying (1 to 2 days). By air-drying at room temperature (typically 20-25° C.) the alcohol and a major part of the water are removed from the cellulose. The drying can also be carried out under vacuum or in a climatic chamber. After drying the bacterial cellulose can still contain glycerin with a content between 0.1 and 10% by weight, with an indicative value of 1.5% by weight. Due to the hygroscopic nature of glycerin it is possible that there is still water present in the bacterial cellulose.

Within the scope of the invention, a molded body is intended to mean a physical object having any possible shape. In the simplest case, this can be a virtually two-dimensional, flat object (similar to a material strip). This is also intended to mean more complicated, three-dimensional shapes such as cylindrical tube sections up to more complex shapes, for example heart valves.

The bacterial cellulose treated using the method according to the invention can now be stored, wherein the desired anti-inflammatory properties and the compatibility of the material are retained. For the case in which the optional step ii) is omitted, the bacterial cellulose surprisingly exhibits a swelling capacity that is clearly increased as compared to the non-treated starting material.

Consequently, a further aspect of the invention is related to a molded body made of bacterial cellulose, which is storable and, optionally, has swelling capacity, and which was produced using the above-described method.

Furthermore, it has been shown that the swelling capacity of cellulose can be influenced in a targeted manner by means of the method according to the invention. The invention is based on the finding, in particular, that dried bacterial cellulose, in particular bacterial cellulose from *Gluconacetobacter xylinus*, can be completely rehydrated by means of the special drying process and contrary to previous expert opinion, and the water absorbance capacity can be increased even further by means of the drying process if the optional step ii) is omitted.

The swelling capacity of the entire molded body or parts of the molded body can therefore be adapted to the requirements for the particular application by means of the mechanical pressing in step ii). In other words, regions of one and the same molded body can be varied independently of one another in terms of swelling capacity. The molded body has preferably at least one region with a reduced swelling capacity based on mechanical pressing in relation to an adjacent region of the body.

A further aspect of the invention is related to an implant comprising the aforementioned molded body in entirety or in parts. In other words, the molded body itself can be the implant or is merely one component thereof.

According to one first variant, the molded body is therefore an implant shell. A layer that closes off the entire implant or essential parts of the implant toward the outside therefore comprises the treated bacterial cellulose. The implant shell can be a type of bag or pocket, for example, in which the further components of the implant are located. The very good biocompatibility of the bacterial cellulose prevents complications due to rejection reactions, which is a particularly important aspect when the implant is a cardiac pacemaker or defibrillator stored in the implant shell. The implant shell preferably additionally comprises a separate pocket for accommodating overhanging electrode cables.

EP 2 484 406 A1 and U.S. Pat. No. 7,454,251 describe devices that make it possible to roll up, in a defined manner, an overhanging electrode cable in pacemakers. This rolling-up does not prevent a tissue capsule from forming on the implant, however.

The biocompatible enclosure of the implant makes it possible to prevent massive fibrotic tissue regeneration. In addition, eventual explantation is simplified. The implant shell can also comprise a separate pocket for overhanging electrode leads that may be present.

The implant shell can be produced, for example, in such a way that layers of the treated bacterial cellulose are sutured with a surgical suture. The pacemaker or defibrillator can be packaged in the implant shell, which is rehydrated with a sterile (isotonic) saline solution, shortly before implantation. By means of the implant shell, it is also possible to prevent the electrodes from adhering too strongly in the region of the unit, thereby ensuring that the unit can be more easily replaced. The anti-inflammatory effect of the bacterial cellulose greatly reduces the risk of infection. Optionally, the material of the implant shell can also be a drug carrier, for example for the temporary release of antibiotics, such as rifampicin, minocycline, doxycyline, tetracycline, gentamycin, vancomycin, linezolid and tigecycline, anti-inflammatory agents, such as paclitaxel, prednisolone, dexamethasone, rapamycin, tacrolimus and ciclosporine, growth factors, for example EGF, HGF, TGF, PDGF, VEGF, NGF and G-CSF and cytokines, for example IL-1B, IL-8. A further aspect of the material is that it can be processed dry, sterilized, and then stored for months. In our own trials, it was confirmed that the material retains the very good anti-inflammatory properties thereof even after the special drying.

According to a second variant, the molded body is a component of a heart valve prosthesis, in particular a heart valve leaflet and/or a sealing shell (skirt) between the heart valve leaflets and the stent base body of the heart valve prosthesis. Formed bodies made of bacterial cellulose that have been treated according to the method are therefore suitable for the production of the essential functional components of a heart valve prosthesis. In contrast to conventional heart valves leaflets, which are formed from pericardium, for example, the heart valves according to the invention can be stored in a dry, sterilized manner and do not need to be rehydrated until shortly before implantation. Moreover, the suture diameter, suture thickness and the orientation thereof, the layer thickness and homogeneity of the valve leaflet can be individually set by adjusting the culture conditions or by after-treatment. In other words, the material according to the invention makes it possible to create heart valve prostheses that are individualized and, therefore, substantially more compatible. The heart valve prosthesis can be delivered in a fully pre-assembled state and not with the insertion device and the valve itself delivered separately, as is currently the case with conventional prostheses. Due to the use of cellulose, the size of the device can be drastically reduced overall (from the current size of 18 Fr to 12 to 14 Fr).

Bacterial cellulose pretreated according to step ii) is used for the heart valve leaflet. In addition to the heart valve leaflets, the material can also be used, in particular, for sealing between the native heart valve leaflet and the stent base body, in this case in the form of an inner and/or outer peripheral shell made of the material. The radial seal relative to the vessel wand is greatly improved due specifically to the significantly improved swelling capacity of the material. Current materials used in skirts are not made of materials with swelling capacity, wherein the intention is to seal paravalvular leaks at the skirt by overhanging the material (see, for example, US 2013/0018458 A1). This cannot always be ensured, however, due to the high pressure gradients at the transition from the ventricle to the atrium. In addition, the material that is used poses a risk of inflammation with the associated risk of contamination by bacteria that can trigger endocarditis. The material according to the invention has the property of storing a great deal of water and, in contrast to a hydrogel, of releasing this water in response to mechanical loading. Due to this particular elastic sealing property, paravalvular leakage is prevented, wherein the skirt made of treated bacterial cellulose—as compared to other materials—can be very thin (preferably 0.05 to 0.2 mm) and can have a swelling ratio of min. 1:10. Consequently, the skirt is provided for preventing paravalvular leakage. Herein paravalvular leakages are leakages with the risk of streaming blood leaking between the implant and the wall of the vessel or the heart valve. The skirt is disposed at the luminal and/or abluminal section of the stent base body of the heart valve implant. The luminal section of the stent base body comprises particularly the inner side of the stent, whereas the abluminal section comprises the outer side of the stent. The skirt can comprise sections or partial sections which are not consisting of bacterial cellulose as described herein, but of other materials. It is however also possible, that the entire skirt consists bacterial cellulose, as described herein. If an embodiment of the skirt comprises sections of other materials than bacterial cellulose, then the skirt comprises at least one molded part of bacterial cellulose, as well, which has been treated by the inventive method. The reduced swelling capacity of the molded body is ideally affected by the inventive method, namely the mechanical pressing in step ii).

In an embodiment of the inventive heart valve implant the skirt has a reduced swelling capacity in the luminal section and at least partially increased swelling capacity in the abluminal section. In a further embodiment of the inventive heart valve implant the skirt is disposed at the luminal side of the stent base body. At least one molded body, preferably a number of molded bodies, is disposed, preferably sewn in, between the stent struts and the skirt. The at least one molded body is formed of bacterial cellulose produced by the inventive method and includes sections with an increased swelling capacity. The at least one molded body with an increased swelling capacity is preferably disposed between the stent base body and a skirt made of material with no swelling capacity, wherein the increase of the volume of the swelling molded body is directed radially outwards. The luminal skirt can be made of bacterial cellulose or of other materials, mainly with no swelling capacity, such as polymers, other artificial materials or biological material such as pericard or lung, stomach or gut tissue.

The at least one molded body is preferably disposed between a nodal point of the stent strut structure and the luminally disposed skirt. Preferably a number of molded bodies are disposed adjacent to each other, so that an annular ring is formed in circumferential direction of the skirt. At least one molded part is sewn to the stent strut structure, preferably to the stent struts, and to the nodal points of the stent strut structure, as well. The term nodal point refers to positions of the stent structure where the struts are connected to each other. Ideally the edges and brinks of the molded part are running at least partially on the struts of the stent base body.

The skirt is preferably disposed in the luminal section of the stent base body and has a reduced swelling capacity in the sections disposed below the struts of the stent base body. It is further preferred if the skirt is disposed luminally at an end of the stent base body which is located in proximity to a heart valve and the inflow region of the valve, respectively.

Furthermore the skirt is preferably disposed in the luminal and abluminal sections of the stent base body and is laced in form of at least one ribbon around the struts of the stent base body in an alternating fashion. The ribbon has a reduced swelling capacity in the sections disposed below the struts of the stent base body.

In general, the use of bacterial cellulose according to the method according to the invention in heart valve prostheses has many advantages:

The valve leaflet and/or the skirt can be processed dry.

The heart valve prosthesis produced in this manner can therefore be shipped in a dry, preassembled state and can be stored for a long period of time.

Moreover, the risk of calcification of such a heart valve prosthesis is less, since, in contrast to the prior art, biological tissue prepared with glutaraldehyde is not used for the valve leaflet in this case.

Furthermore, the heart valve prosthesis has a lower risk of inflammation due to the antibacterial properties of the bacterial cellulose.

Percutaneously implantable heart valve prostheses, for example for the mitral valve, have a metallic base body, which is used for anchoring at the implantation site and carries the artificial heart valve leaflet. For example, US 2011/0208298 A1 describes a holding device, which clamps a percutaneous mitral valve between the mitral annulus and the distal end of the natural valve leaflet by means of two clip structures. U.S. Pat. No. 8,252,051 describes a percutaneous mitral valve, in which additional holding structures, in the form of hooks, are mounted on the stent base body. These outwardly bent, hook-shaped projections engage into the surrounding tissue and thereby anchor the valve in the tissue in order to prevent proximal dislocation.

Disadvantages of the aforementioned solutions are the fact that the clip and hook structures do not permit the valve to be small and compact. Therefore, in the aforementioned embodiment of the prior art, for example, it is necessary to lengthen the valve on the distal end to the extent that the clip structure protrudes beyond the distal end of the natural valve leaflet. In addition, the clip structure necessitates a larger diameter of the curved valve, which cannot be minimized further. The holding structures in the form of hooks in U.S. Pat. No. 8,252,051 B can damage the aortic valve or the Ramus circumflexus if tissue penetration is too deep or due to implant erosion. As is the case according to the invention, however, if the molded body comprises barbs on an outer side of the stent base body thereof, an adhesive connection for preventing dislocation of the valve can be ensured without the aforementioned disadvantages.

The barbs preferably have a length of <0.5 mm, in particular a length in the range of 0.1 to 0.3 mm.

A further aspect of the invention relates to a catheter comprising a heart valve prosthesis, which has at least one molded body made of bacterial cellulose according to the method according to the invention, wherein the heart valve prosthesis is mounted on the catheter in the dried state.

According to a third variant, the molded body is an outer shell and/or an inner shell of a stent graft made of bacterial cellulose according to the method according to the invention. The bacterial cellulose treated according to the invention is therefore also suitable for producing a self-sealing stent graft. According to the prior art, endovascular stent grafts are implanted with an exact fit, for example into the aorta, in order to treat aneurysms. In ten to forty percent of cases, these exhibit leakage, with the risk of the aneurysm rupturing. A significant portion of these patients exhibit leaky points at the transition of the native aorta to the stent graft.

These so-called type I leaks are caused by the graft slipping or are due to the individual anatomy.

A method that is intended to solve this problem is described in US 2013/0197622 A1. In this case, a swellable hydrogel is placed in a cuff about the distal or proximal end of the stent graft, which swells after coming into contact with moisture or after addition of a foaming agent. The use of hydrogels has the disadvantage, however, that these must be enclosed with an additional membrane. In addition, the biocompatibility and long-term mechanical stability of the material is questionable. Finally, reversible swelling is not possible.

If outer and/or inner shells of the stent graft are formed of the bacterial cellulose treated according to the invention, however, a material is then available that is reversibly swellable, biocompatible, and non-degradable, and avoids all the aforementioned disadvantages. It has been shown that bacterially synthesized cellulose is particularly suitable therefor. This can be synthesized by *Gluconacetobacter xylinus* in tubular form by the metabolization of a glucose-containing nutritive solution and can then be specially dried. The high-purity cellulose fiber tubes that are formed have mechanical properties, in the moist state, that are similar to those of blood vessels and can easily withstand pressures of 120 mm of mercury. For production, a fleece made of the cellulose is sutured with a stent, or the fleece is generated integrally with the stent.

According to a preferred embodiment, the inner or outer shell comprises annular sections, which are disposed on the axial ends of the stent graft and exhibit a greater swelling capacity than do sections of the shells located between the two ends. In other words, the swelling capacity is increased at the two ends of the stent graft, for example by increasing the layer thickness, and/or the center sections of the shell were pretreated as described in step ii) of the method. After the cellulose is moistened, the shells are thickened at the two ends and thereby close any leakages that may occur at the distal and proximal end of the stent graft. The other sections of the inner or outer shell do not swell, since the layer thickness is thinner or due to a modified drying scheme (step ii), or do not swell to the same extent, and form the tube-like blood vessel replacement. The material for the inner and outer sleeve can be processed in the dried state and is very thin, and can therefore be used for stent grafts and with a particularly small diameter. Microstructuring can be implemented on the luminal side in order to accelerate the re-endothelialization. This can be impressed with a dimension of 1 to 10 μm directly in the synthesis of the bacterial cellulose layer (see also US 2012/0053677 A1).

According to a fourth variant, the molded body is a covering of a stent. According thereto, the material according to the invention is used to produce a stent that is covered by a biocompatible fleece comprising bacterial cellulose.

Such a stent graft comprising a fleece made of bacterial cellulose and/or having annular sections made of bacterial cellulose having an increased swelling capacity has a number of advantages:

When annular sections made of swellable bacterial cellulose are used, a good form-fit connection between the vessel wall and the stent graft is obtained.

Due to the use of a fleece made of bacterial cellulose, the biocompatibility of the stent graft is increased and the potential for inflammation is reduced due to the antibacterial properties of the cellulose.

The structured surface of the fleece made of bacterial cellulose promotes good re-endothelialization.

Moreover, a stent graft comprising a fleece made of bacterial cellulose can be compressed to a small diameter. The stent graft can therefore be gently brought to the implantation site using a catheter having a relatively small outer diameter, and can be implanted there.

So-called covered stents comprise a stent base body covered with a polymer (e.g., polyurethane or polytetrafluorethylene), which is stretched between the stent struts as a membrane or by means of hot-embossing, or is applied by means of electrospinning (see, for example, EP 2 380 526 A2 or EP 0 866 678 B1). In addition, it is known that bacterial cellulose produced by fermentation is suitable for use as fleece for covering stents. In this case, the cellulose is deposited directly between the stent struts in a special bioreactor (see EP 1 569 578 B1). A disadvantage of the use of polymer films is greatly reduced biocompatibility and an increased risk of inflammatory reactions. Bacterial cellulose, on the other hand, is highly biocompatible, but is very brittle in the untreated, dried state and can become damaged during the crimping process.

It has been shown, surprisingly, that the above-described after-treatment with an alcoholic glycerol solution imparts bacterial cellulose with mechanical properties in the wet state that are similar to those of the natural vessel wall. Moreover, it has been shown that the swelling behavior of the bacterial cellulose can be controlled by immersion in diluted alcoholic glycerol solutions. The treated bacterial cellulose is also no longer brittle and can be processed, by squeezing, to form a very thin cellulose fleece, which can be placed tightly around the stent frame. This thin membrane, in the dried state, requires only that the implant be thickened to a negligible extent and thereby simplifies implantation. In addition, it has been shown that the special after-treatment with glycerol imparts flexibility to the cellulose, thereby enabling the cellulose to be folded during crimping. After the implant is moistened, the cellulose swells to an adjustable thickness and thereby forms an extremely tension-resistant, highly hydrated fleece, which permits repopulation with endothelial cells and is simultaneously pressure-tight. Moreover, the bacterial cellulose reduces the risk of an inflammatory reaction and is biocompatible. In order to accelerate re-endothelialization, microstructuring of the luminal side can be implemented, as described above.

According to a fifth variant, the molded body is a vascular patch. According to the prior art, patches for covering relatively extensive vascular damage are woven out of plastic, such as polyester, or are cast of polytetrafluorethylene. In addition, the woven structures are additionally sealed with collagen in order to prevent leakage caused by the web structure.

This results in the disadvantage that the seal integrity of seams cannot be ensured with PTFE, and, with polyester, biocompatibility is reduced and the susceptibility to inflammatory reactions is therefore increased.

According to a further variant, the molded body is an occluder, which is implanted in the heart by means of a catheter in order to treat/close a patent foramen *ovale*. Such an occluder has the shape of a small umbrella and closes the patent foramen *ovale*.

According to a further variant, the molded body is an artificial tendon.

The bacterial cellulose treated according to the invention therefore provides an easily swellable, self-sealing, and biocompatible material for producing an improved vascular patch or material for use in heart valve prostheses. It has been shown that bacterially synthesized cellulose is particularly suitable for these purposes.

General Procedure for Producing a Molded Body from Storable and Swellable Bacterial Cellulose It is known that bacteria of the species *Gluconacetobacter xylinus* can deposit cellulose on gas-permeable silicone membranes by metabolizing glucose-containing nutritive media. The depositing preferably takes place on the silicone membrane. The silicone membrane can be configured as a flat substrate, for example, or in the form of a three-dimensional hollow body, in order to produce the cellulose in the shape of a tube, for example.

The silicone membrane is modified in a particular manner in order to produce cellulose layers having different material thicknesses, in order to prevent tension peaks at critical points in the event of strong material loading, for example. In the production of heart valves it can be advantageous, for example, to produce the valve leaflet required therefor such that more material is present in the regions of highest mechanical load than in regions having a lower mechanical load. This can be achieved by using a modified silicone membrane, the thickness of which varies. In this manner it is possible to control the diffusion of oxygen as a function of the layer thickness. Due to the reduced oxygen concentration in the regions of the thicker silicone membrane, the locally present bacteria can only produce cellulose to a lesser extent, while material is deposited to a greater extent in regions of the silicone membrane having a thin layer thickness.

Figure 9:
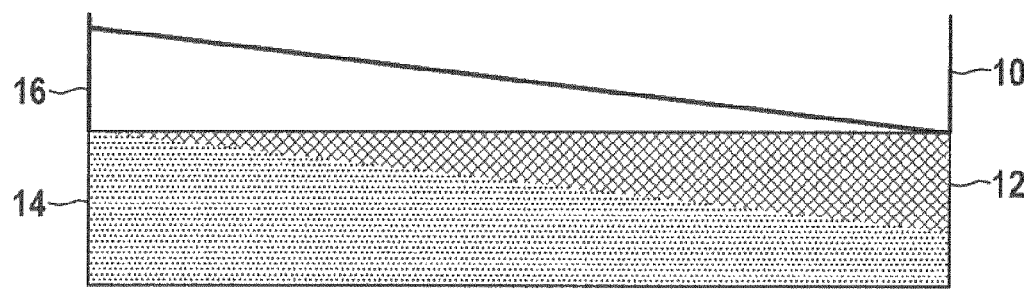
FIG. 9 shows a schematic depiction of a culture vessel, with which bacterial cellulose having different material-layer thicknesses can be separated out.

FIG. 9 presents a schematic illustration of a culture vessel 10, which is suitable for producing cellulose layers 12 having different thicknesses. According to one embodiment, 150 ml of a Hestrin/Schramm nutritive solution 14 are placed in the flat culture vessel 10 and are inoculated with 4 ml of an inoculation medium (*Gluconacetobacter xylinus*). The culture vessel 10 is covered with a gas-permeable silicone membrane 16 without enclosing air. The culture vessel 10 is placed in an oxygen-enriched atmosphere in order to promote the aerobic growth of the bacteria on the silicone membrane 16. During incubation at 30° C. for several days, a cellulose layer 12 becomes deposited, which has the greatest layer thickness at the point where the silicone membrane 16 is the thinnest. Depending on the layer thickness of the silicone membrane 16 and the incubation period, layer thicknesses of the cellulose layer 12 in the range of 2 to 10 mm or more can be generated.

In general, the control of the layer thickness of the cellulose layer 12 allows a design of layers which have a predetermined thickness. The predetermined thickness can be set to such an extent that working methods such as cutting, milling or laser ablation preferably of frozen or freeze dried cellulose can be applied to the material with a greater flexibility than, for example, to biological material, which is significantly thinner and requires a very precise handling and cutting which is technically difficult to implement. Consequently the control of layer thickness is advantageous in terms of a high accuracy of fit, stability and flexibility of the bacterial cellulose layer 12.

Furthermore, the thickness of the silicone membrane 16 can be varied across its whole part in order to control not only the thickness of the bacterial cellulose layer 12, but also the form of the molded body. With other words, the form of the silicone membrane can be used to control the thickness of the molded body in different sections. By varying the thickness in different parts the silicone membrane 16 the cellulose production of the bacteria can be controlled. It will be stronger in positions where the silicone membrane has a lower thickness, and weaker where the silicone membrane has a higher thickness. Consequently, if a certain form of the silicone membrane 16 is provided, the molded body will have a corresponding reversed form.

Thus, the silicone membrane can be used as a positive image for the form of the cellulose body, so that the molded form presents a negative image of the form of the silicone membrane 16. This way the design of the silicone membrane 16 can be advantageously used to control the form of the molded body. Consequently a desired form of an implant comprising bacterial cellulose, or at least of a part of it, can be designed by way of controlled bacterial growth.

Composition of the Herstrin/Schramm Nutritive Solution:
Disodium hydrogen phosphate 2.7 g
Glucose 20 g
Soybean peptone 5 g
Yeast extract 5 g
Citric acid 1.15 g
Water 1 l
pH 6.0

A culture vessel according to the initially described embodiment of the invention permits targeted control of the molded body made of bacterial cellulose. Given that the thickness can be varied in a targeted manner as described above, it is possible to produce inhomogenous molded bodies as needed. These can be flexible sheets of a heart valve prosthesis, for example. The zones having high mechanical load, where the sheets are fastened on the support body of the prosthesis or on a sealing skirt, can be made thicker and are therefore more highly loadable. By contrast, the flexible ends of the sheets are made thinner.

A further application of the molded bodies made of bacterial cellulose is that of artificial tendons. Optionally, the bacterial cellulose can also be processed to form a composite material by admixing further materials, for example polyacrylates, polyesters, polyamides, polyurethanes, polylactates, chitosan, and starch-containing plastics.

The cellulose layers 12 that form are washed with water and are subsequently washed in a non-pyrogenic manner in an alkaline cleaning solution. For the case in which the cellulose should have high strength but low swelling capacity, the cleaned cellulose layers 12 are mechanically pressed to a layer thickness of 0.07 to 0.1 mm. The layers are subsequently air-dried. These layers are incubated in a mixture of 20% by weight of glycerol, 20% by weight of water, and 60% by weight of isopropanol for 1 to 3 h and are subsequently mounted in a support frame and are dried.

The cellulose can be processed and stored in the dry state without losing the positive characteristics thereof. The anti-inflammatory properties and the very good biocompatibility are retained, as is the high mechanical strength of the material.

The particular swelling capacity of the non-pressed but treated bacterial cellulose was investigated more closely using 2 mm-thick layers of the material. The samples were initially completely hydrated in water (12 h) and weighed.

The samples were then incubated in an incubation mixture comprising, for example, 30% by weight of glycerol and 56% by weight of an C1-C3 alcohol and 14% by weight of water for 2 h, removed, air-dried for 24 h, and weighed. Next, the samples were rehydrated in water for 12 h and weighed. The additional water uptake, in percent, compared to the non-treated material is presented in the final column of table 1.

| Sample | Hydrated (mg) | Dry (mg) | Rehydrated (mg) | % |
|---|---|---|---|---|
| 1 | 804 | 136 | 1000 | 124.3 |
| 2 | 746 | 138 | 956 | 128.1 |
| 3 | 681 | 116 | 834 | 122.4 |
| 4 | 793 | 131 | 922 | 116.2 |
| 5 | 797 | 126 | 827 | 103.7 |
| 6 | 755 | 125 | 843 | 111.6 |
| 7 | 732 | 127 | 874 | 119.3 |
| 8 | 771 | 112 | 874 | 113.3 |
| 9 | 686 | 108 | 768 | 111.9 |
| 10 | 627 | 123 | 720 | 114.8 |
| 11 | 678 | 143 | 848 | 125.0 |
| 12 | 738 | 111 | 1140 | 154.4 |
| 13 | 617 | 122 | 761 | 123.3 |
| 14 | 695 | 127 | 977 | 140.5 |
| 15 | 726 | 127 | 877 | 120.7 |
| Mean | 723 | 124.8 | 881.4 | 122 |

It is evident that the swelling capacity was significantly increased under the aforementioned experimental conditions.

Figure 10:
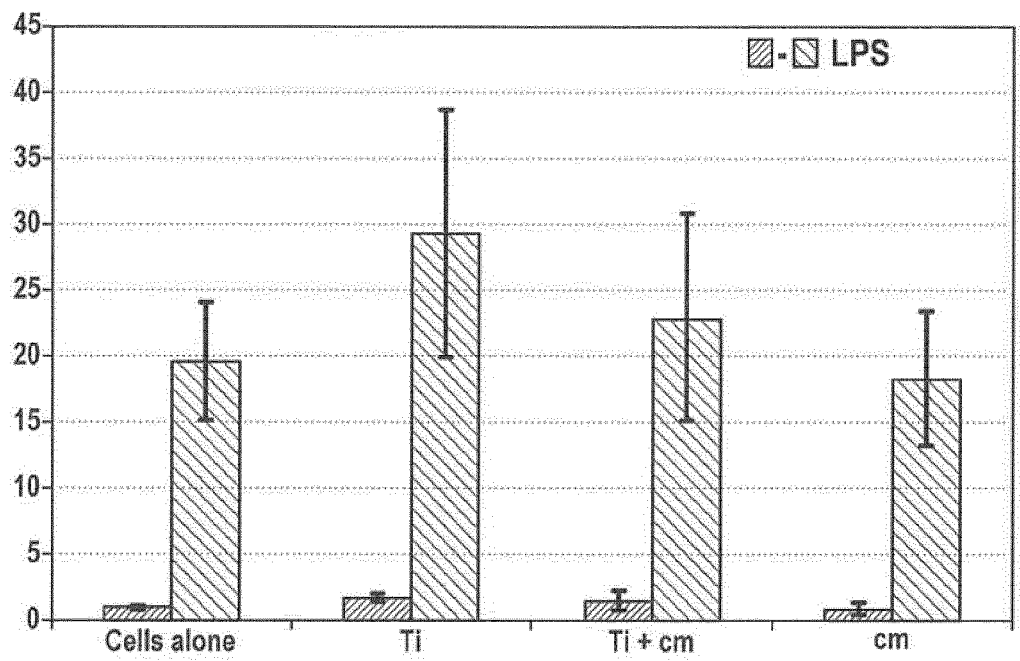
FIG. 10 shows a comparative depiction of the NF-kB activity in THP-1 cells.

The treated cellulose was investigated in an in vitro assay in order to investigate the anti-inflammatory properties (see FIG. 10). A titanium surface (labelled "Ti" in the graph), which often used in pacemakers, was used as the reference value. The activation of the cells in the absence of titanium (cells alone) or the treated cellulose (cm) was measured as the reference value. To this end, the corresponding surfaces were cultivated in a special sample chamber together with mononuclear cells (THP-1 cells), which indicate the activity status of NF-kB, an inflammatory marker. Each test series was carried out in triplicate. The cells were additionally activated with LPS (lipopolysaccharide), thereby simulating an inflammatory reaction (the bar on the right in each case). Next, the activation of NF-kB was quantitatively evaluated. The NF-kB activation of the THP-1 cells in the presence of the treated cellulose (18 a.u.) was found to be clearly reduced as compared to the titanium surface (28 a.u.). In this case, the NF-kB activation by the treated cellulose is just as great as the negative control. This illustrates once more that the treated cellulose has a very mild effect on the NF-kB activation of the THP-1 cells and, therefore, inflammatory reactions are practically unexpected. The treated cellulose will therefore likely only trigger a greatly diminished immune response in the human body and the immunologically active cells will retain their immunocompetence.

A few specific applications of the treated bacterial cellulose are described in the following.

Implant Shell for a Cardiac Pacemaker

According to this embodiment, an implant shell 20 was produced from the treated bacterial cellulose, and was used to accommodate a cardiac pacemaker 22 (see FIG. 1).

In accordance with the above-described general procedure, three layers of bacterial cellulose each having a layer thickness of 0.2 mm were dried. The layers were sutured to one another to form the implant shell 20, using a polymer thread (PTFE, size 5-0) and a 0.3 mm suture needle, using a shell scalloping stitch. The thusly sutured implant shell 20 made of cellulose can be sterilized and stored in the dry state.

The pacemaker 22, with the electrodes attached, is rehydrated and packaged by means of a sterile (isotonic) saline solution shortly before implantation. FIG. 1 shows—in a highly schematic depiction—the completed implant shell 20 in a top view, said implant shell being used to accommodate the pacemaker 22. The direction of insertion is indicated by the arrow.

The overhanging electrodes are wound up in a separate pocket 24 of the implant shell 20.

Transcatheter Heart Valve Prosthesis

According to this embodiment, components of a transcatheter heart valve prosthesis were produced from the treated cellulose.

The cardiac septum separates the human heart into two halves, i.e. into a right ventricle and a right atrium, and into a left ventricle and a left atrium. Four heart valves are located between the ventricles and the atria. Blood that is anoxemic but rich in carbon dioxide flows first through the tricuspid valve into the right atrium and, from there, into the right ventricle. The tricuspid valve is a tricuspidate valve and is also referred to as an atrioventricular valve. From the right chamber, blood flows through the pulmonary valve into both lungs, where the blood is re-enriched with oxygen. The pulmonary valve is a so-called semilunar valve. The oxygen-enriched blood now leaves the lungs, enters the left atrium, and is pumped through the mitral valve, which has the form of a bicuspidate atrioventricular valve, into the left chamber.

Finally, the blood flows out of the left ventricle, through the aortic valve, and into major blood circulation. The aortic valve, similar to the pulmonary valve, is a semilunar valve.

If a patient has heart valve defects, it can be assumed that the functionality of these heart valves can worsen continuously over time. The replacement of heart valves that have stopped functioning with heart valve prostheses has since become second only to the coronary bypass operation as the most common operation performed on the human heart. An ideal heart valve replacement should have an unlimited service life, should allow blood to flow unobstructed in the vessel, should not result in heart valve-related complications such as increased thrombogenicity or susceptibility to endocarditis, should not pose any risks inherent to prostheses, such as valve-related defects, should permit easy implantation, and should be quiet.

Minimally invasive techniques and transcatheter heart valve prostheses have since been developed, in which the new heart valve is brought to the implantation site by means of a catheter system and is anchored there. The anchoring in the vessel wall is implemented by means of a support structure for the actual heart valve, for example by means of a metallic mesh having a design and material selection similar to that of a stent, which is therefore also referred to in the following as a stent base body. The stent base body can be self-expanding, or can be expanded using a balloon catheter.

Conventional transcatheter heart valve prostheses therefore comprise a stent base body, which can be expanded from a first size, which is configured for minimally invasive insertion, into a functional, second size. The actual heart valve is fixed on this support structure, wherein said heart valve initially assumes a first shape, which is configured for minimally invasive insertion and which can be expanded, over the course of implantation, into the functional, second shape. For example, the heart valve is formed of a plurality of flexible sheets, each of which opens or closes according to the bloodflow forces acting thereon. Such a transcatheter heart valve prosthesis comprising a biological cardiac valve is described in EP 1 267 753 B1, for example.

Figure 2:
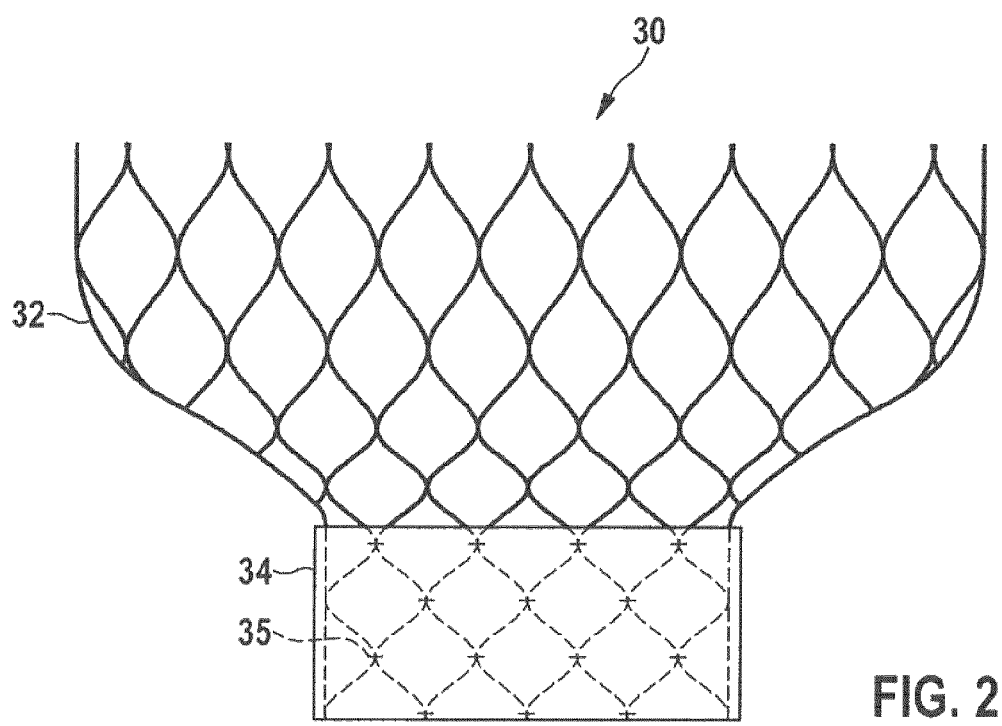
FIG. 2 shows a side view of a further embodiment of the molded body according to the invention, in the form of a heart valve prosthesis.
Figure 3:
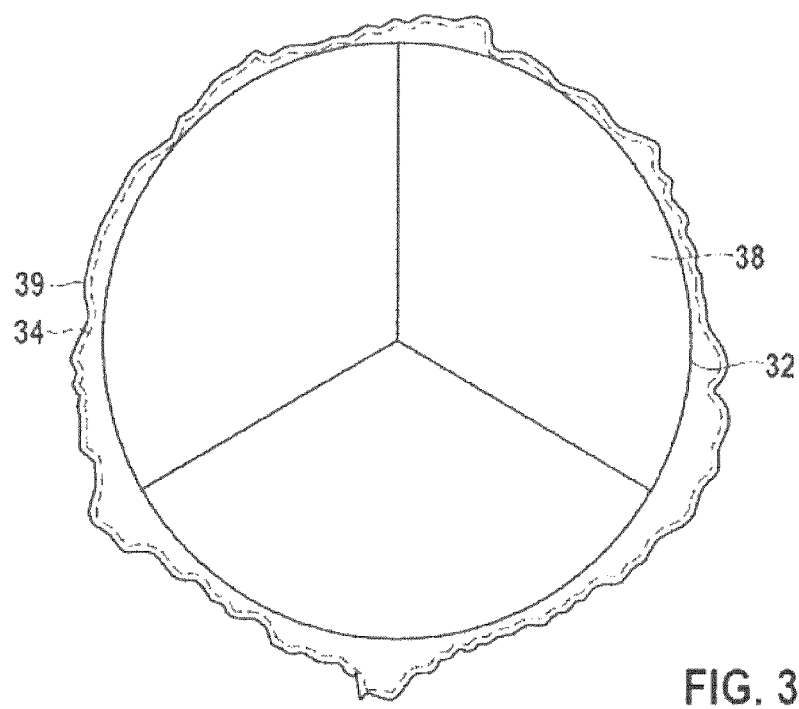
FIG. 3 shows a top view of the heart valve prosthesis in FIG. 2.

A schematic side view of an expanded transcatheter heart valve prosthesis 30 is shown in FIG. 2. The embodiment depicted in FIG. 2 is a heart valve prosthesis that is intended for implantation as a replacement of the natural mitral valve. The stent base body 32 comprising metallic struts is used for anchoring at the implantation site. In this case, a peripheral sealing shell (also referred to as the skirt 34) made of the treated bacterial cellulose is fastened on the stent base body 32 by means of suturing (over-and-over sutures 35 of Teflon thread, for example), wherein said sealing shell is adjoined here, without transition, by the cardiac valve leaflets 38 (see FIG. 3), which are made of the same material. In order to build this complex molded body comprising the skirt 34 and the cardiac valve leaflets 38, cellulose layers that have been dried according to the above-described synthesis procedure are cut to fit. A strip of the swellable cellulose material that is approximately 1.5 mm wide and approximately 0.2 mm thick is used for the skirt 34. After implantation and contact with blood, the thickness of the skirt 34 increases multifold (up to 0.5 mm) and seals the contour of the annulus 39, which is non-uniform due to the calcified natural valve. The heart valve prosthesis is then mounted on a catheter and sterilized.

Figure 4:
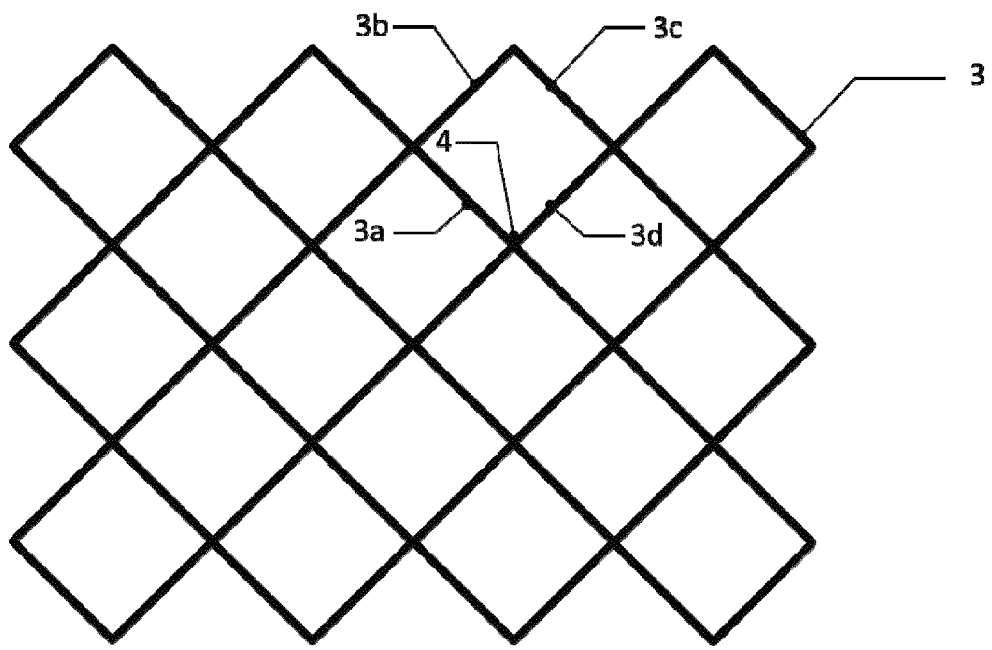
FIG. 4 shows a simplified representation of a stent structure with stent struts and nodal points.
Figure 5:
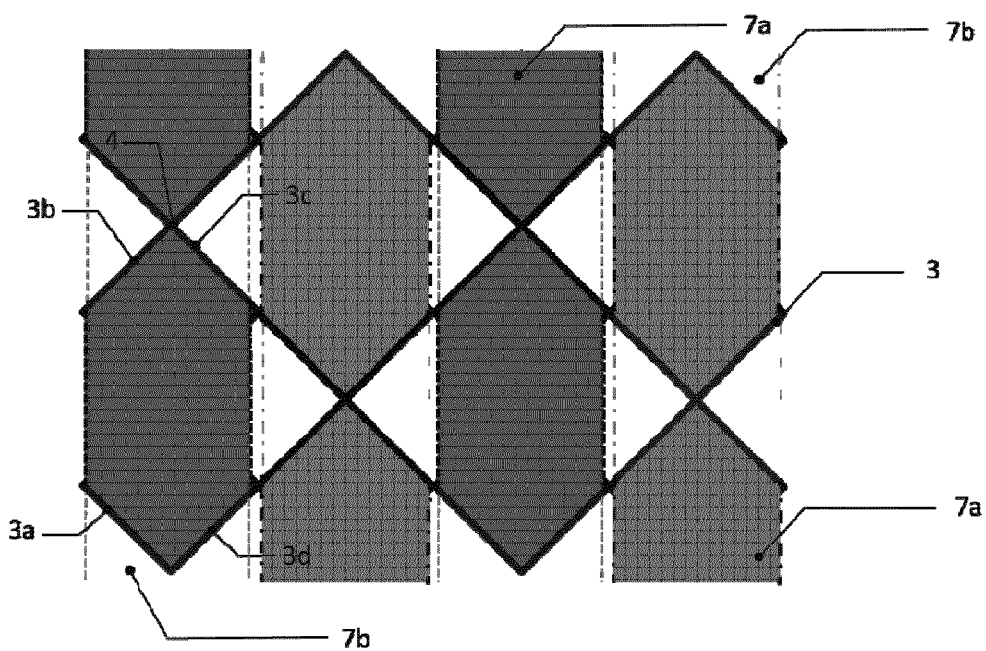
FIG. 5 shows a view of a section of a stent structure wherein stripes of bacterial cellulose are running above and below the stent struts.

FIG. 4 shows a partial view of a structure of a stent base body with struts 3a, 3b, 3c, and 3d. The adjacent struts 3a, 3b, 3c, 3d are connected via a nodal point 4. The stent struts form a rhombus-like opening. This stent structure can be advantageously used for disposing strips of bacterial cellulose in an interwoven pattern. The strips can be sewn to each other and/or to the stents. In one embodiment, as shown in FIG. 5, the strips are passed over and under the nodal points 4. Thereby a first surface 7a is formed, which is located above the stent struts 3a, 3b, 3c, 3d and the nodal points 4, and a second surface 7b, which is located below the named struts and nodal points. The bacterial cellulose can be treated by mechanical pressing in such a way that the sections of the material below the named struts and nodal points have a reduced swelling capacity. Furthermore the strips of cellulose can be disposed in such a way that the edges of the strips are overlapping each other for a small part, which is indicated by the dashed lines. The overlapping is advantageous because it helps preventing a flow through.

Figure 6:
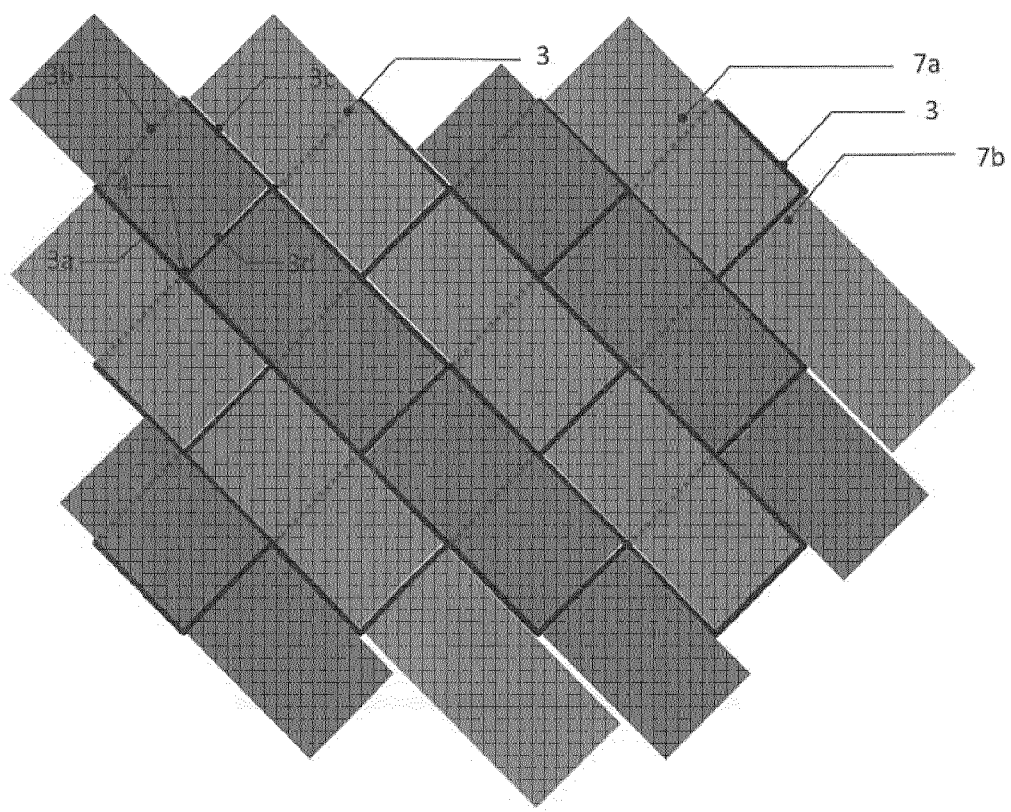
FIG. 6 shows a view of a section of a stent structure wherein strips of bacterial cellulose are running above and below the stent struts.

FIG. 6 shows a further embodiment wherein the strips are interweaved into the stent structure by passing a first strip 5a above and below the struts 3a and 3c and a second strip 5b above and below the struts 3b and 3d. Struts below the cellulose are shown as dashed lines, struts above the cellulose are shown as thick lines. As in FIG. 5, surfaces 7a and 7b of the stripes are shown which are located above and below the stent structure, respectively. The interweaving of the bacterial cellulose in the stent structure results in a constant alternation of the surfaces 7a and 7b.

Figure 11:
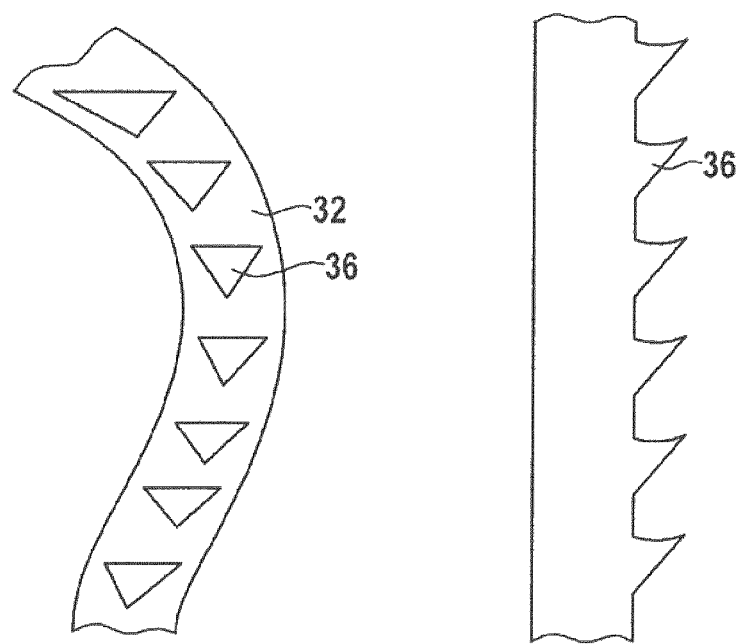
FIG. 11 shows a top view and a side view of sections of a strut comprising a plurality of barbs.

In the case of a mitral valve prosthesis, small barbs 36 (having a length of approximately 0.1 to 0.3 mm) are optionally mounted on the outer strut surface on the stent base body 32, as shown in FIG. 11, in a top and side view of sections of a strut. These barbs are configured such that they do not affect the sutures 35 required to produce the valve. Since a large number of these small barbs 36 can be mounted on the outer side, the adhesive connection for preventing dislocation of the valve is ensured. The barbs 36 can be mounted on the entire outer side, in particular in the region of the mitral annulus and the native valve cusps. As a result, the retaining force can be distributed around the entire circumferential length of the valve. In order to produce the barbs 36, an electropolished stent base body can be drawn on a steel mandrel and the outer surface of the struts can be provided with barbs 36 by means of necking tools.

In order to ensure that the crimped stent can unfold nevertheless, these barbs can be covered with a biocompatible and rapidly dissolvable material, which temporarily covers the barbs 36.

The material dissolves in the bloodstream within seconds to minutes after the stent base body is unfolded. Materials that are suitable therefor are completely hydrolyzed, low- to medium-molecular polyvinyl alcohol or hydrolyzed silk protein, for example.

The valve cusps 38 are produced from the cellulose, which has been pretreated by means of mechanical pressing. The valve cusps 38 and the skirt 34 are sutured to one another or are already a component of a common formed body. In the latter case, only the sections of the common formed body that are intended to form the valve cusps 38 are pretreated by mechanical pressing according to step ii) of the method. The mechanical loadability of bacterial cellulose can be decisively increased by means of a variable layer thickness. For example, a heart valve constructed of bacterial cellulose can have an increased material thickness at the commissures, while the material at the free ends of the valve cusps can be configured to be thinner and, therefore, better capable of moving. As a result, mechanical loads at the commissures are weakened, without limiting the valve movement to an excessive extent. This is not possible, in particular, when porcine or bovine pericardium is used. In this case, the valve cusps have homogeneous layer thicknesses, which can result in mechanical overloading at the seams.

Since the material can be processed and stored in the dry state, and since the material can be produced in different layer thicknesses, with different swelling capacities and mechanical strengths, it is possible to construct the entire transcatheter heart valve prosthesis, for example a transcutaneous aortic valve, out of bacterial cellulose.

The skirt 34 on the proximal end of the valve itself minimizes unwanted leakage flows. To this end, the specially treated cellulose of the skirt 34 is sutured onto the proximal struts of the stent base body 32, wherein these have the property of swelling by absorbing water. This swelling induces a minimal proximal displacement of the stent base body 32 in the direction of the atrium, and so, in the case of a mitral valve, the barbs 36 finally engage in the surrounding native tissue. In the embodiment of a heart valve prosthesis for use as a mitral valve replacement, a skirt is therefore installed in the proximal outflow region of the heart valve prosthesis in order to prevent leakage flows.

An embodiment of the invention as a heart valve prosthesis for replacing the natural aortic valve (not illustrated) is also advantageous. Such an embodiment is substantially similar to the embodiment of a heart valve prosthesis for use as a mitral valve replacement as shown in FIG. 2. In the case of a heart valve prosthesis for use as an aortic valve replacement, the proximal part is the inflow region of the valve. The open and closed position of the valve cusp is correspondingly opposed to the embodiment of a heart valve prosthesis for use as a mitral valve replacement. Likewise, in the case of a heart valve prosthesis for use as an aortic valve replacement, a skirt made of swellable bacterial cellulose is advantageously disposed in the proximal region of the support stent in order to prevent leakage flows in the inflow region.

The valve cusps made of bacterial cellulose are fastened on the support stent by means of the skirt and, optionally, can be configured such that said valve cusps have a greater thickness and, therefore, greater mechanical stability in the region of the fastening on the skirt/support stent than in the flexible region in the center of the flow channel formed by the heart valve prosthesis.

Stent Graft

Figure 7:
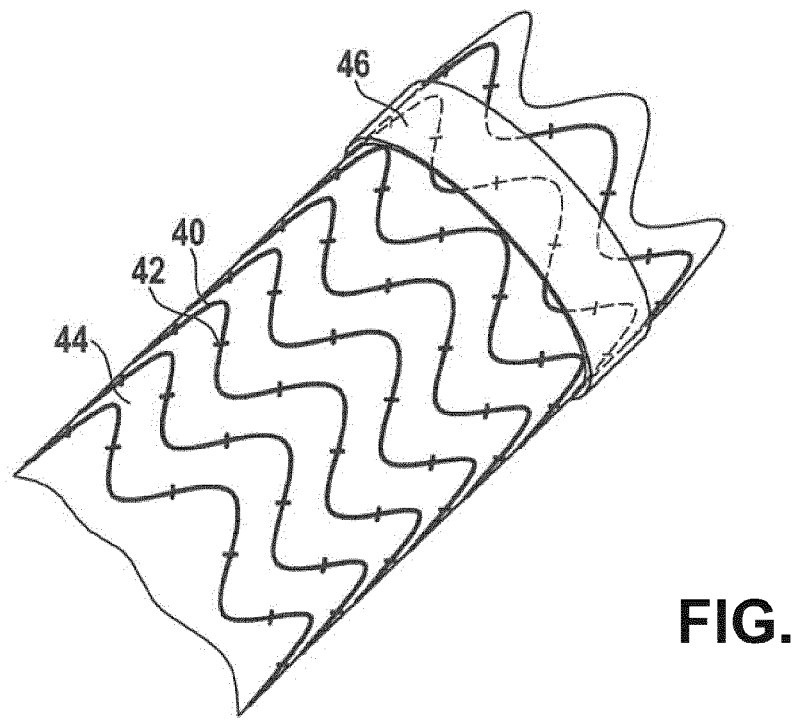
FIG. 7 shows a further embodiment of the molded body according to the invention, in the form of a stent graft.

According to this embodiment, an inner and/or outer shell of a stent graft is produced from the specially treated bacterial cellulose (see FIG. 7). A stent graft is the combination of a stabilizing support frame, which is also referred to in the following as the stent base body, and an artificial blood vessel (vascular prosthesis). The implantation of a stent graft is an endovascular operation. The stent graft is used, in particular, in order to exclude aneurysms from the bloodstream. In the present case, the stent base body is provided with an inner shell made of treated cellulose.

As described above, tubes can be made from cellulose and can be treated. In this case, a microstructure can be impressed on the luminal side of the inner shell during the cellulose synthesis, because the fiber orientation of cellulose bacterially synthesized on the inner side of silicone tubes exhibits a preferred direction along the longitudinal axis of the silicone tube.

This preferred direction can be further enhanced by providing the silicone tube with longitudinal grooves on the inner side that have a groove spacing of 0.5 to 12 m, preferably 1 to 10 m and a groove depth of 2 to 5 m.

The stent base body 40 preferably self-expanding is fastened on the inner shell 44, which was produced using cellulose, by means of a surgical suture material 42. Strips 46, which are also tubular and have a width of 1 to 2 cm, are then fastened on the outer side at both ends by means of suturing. This strip 46 made of cellulose has a greater swelling capacity as compared to the inner shell 44 and therefore makes it possible to seal leaky points after implantation without substantially increasing the diameter of the implant during implantation.

Vascular Patches

According to a further embodiment, the molded body made of the treated cellulose is a vascular patch.

In medicine, a vascular patch is understood to be a piece of foreign material that is used in surgical procedures to close an unwanted opening. A patch is always used whenever an opening cannot be closed without complications by means of a simple seam. One example of regular use are heart surgeries in which septal defects, for example, are closed at this time by means of pericardial or PTFE patches. A patch is also used for the vascular surgical widening of a blood vessel (arterial and venous) or for covering defects on the blood vessels. The patch is sutured into the opened vessel, for example to prevent stenoses caused by seams, or for purposes of widening. In the present case, the patch is produced of the bacterial cellulose treated in the above-described manner.

Covered Stent

Figure 8:
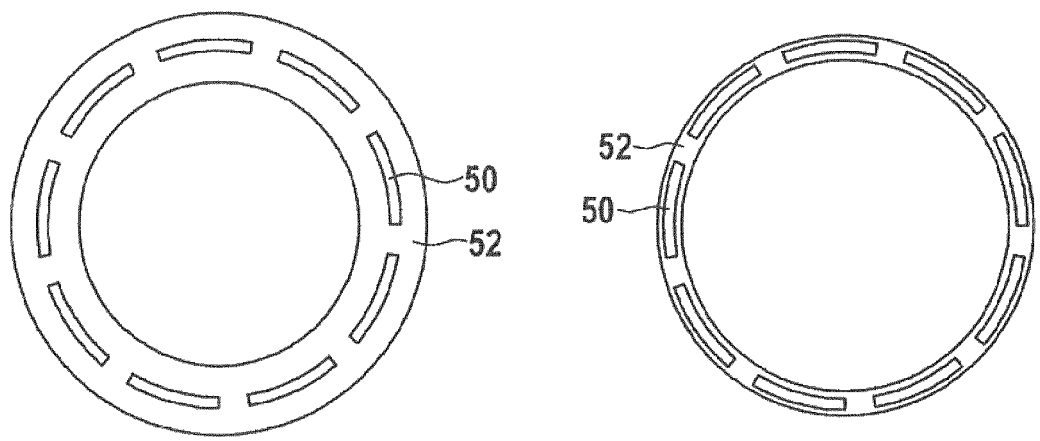
FIG. 8 shows a further embodiment of the molded body according to the invention, in the form of a stent.

According to a further embodiment, a stent is covered by a fleece comprising the treated bacterial cellulose (FIG. 8).

A stent (which is also referred to as a vascular support) is a medical implant that is inserted into hollow organs, in order to hold these open. The stent is usually a small lattice framework in the shape of a small tube composed of metal or plastic fibers, which is also referred to as a stent base body in the present case. 150 ml Hestrin/Schramm nutritive solution having the aforementioned composition are placed in a cylindrical culture vessel and are inoculated with 4 ml of an inoculation solution (*Gluconacetobacter xylinus*). A gas-permeable silicone tube carrying, on the surface thereof, the stent base body to be covered is hung in the culture vessel. The inner side of the tube is acted upon with pure oxygen in order to promote the aerobic growth of the bacteria on the silicone surface. Next, cultivation is allowed to take place at 30° C. until the necessary layer thickness is reached. The objective is to obtain a layer thickness of 2 to 5 mm. The cellulose layers that form are washed with water and are subsequently washed in a non-pyrogenic manner in an alkaline cleaning solution.

The purified cellulose fiber tubes are pressed to a layer thickness of 0.07 to 0.1 mm by means of crimping. Next, the tubes are mounted on a mandrel and are air-dried. These layers are incubated in a mixture of 20% by weight of glycerol, 20% by weight of water, and 60% by is weight of isopropanol for 1 to 3 h and are subsequently mounted on a mandrel once more and are dried.

FIG. 8 shows a schematic view of a stent 50 covered with bacterial cellulose, before drying (on the left) and after drying (on the right). The drying reduces the thickness of the cellulose layer 52 multifold.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

The invention claimed is:

1. A method for producing a storable and swellable molded body made of bacterial cellulose, wherein the method comprises steps of:
   providing a molded body of the bacterial cellulose, the bacterial cellulose in the molded body consisting of fibers of bacterial cellulose without foreign polymers;
   treating the molded body with a treatment solution comprising
   20% by weight to 50% by weight of glycerol and 50% by weight to 80% by weight of a C1-C3-alcohol/water mixture; and
   drying the treated molded body.

2. The method according to claim 1, wherein the treatment solution contains a water portion of at most 20% by weight.

3. The method according to claim 1, wherein the molded body is at least a section of an implant shell of an implant.

4. The method according to claim 3, wherein the implant is a cardiac pacemaker or a defibrillator which is stored in the implant shell.

5. The method according to claim 4, wherein the implant shell is a separate pocket for accommodating electrode cables.

6. The method according to claim 1, wherein the molded body is at least a section of a heart valve leaflet of a heart valve prosthesis and/or at least a section of a sealing shell.

7. The method according to claim 6, wherein an outer side of a stent base body of the heart valve prosthesis comprises barbs.

8. The method according to claim 1, wherein the molded body is at least a section of an outer shell and/or inner shell of a stent graft.

9. The method according to claim 8, wherein the inner or outer shell comprises annular sections, which are disposed on the axial ends of the stent graft and exhibit a greater swelling capacity than do sections of the shells located between the two ends.

10. The method according to claim 1, wherein the molded body is a coating of a stent.

11. The method according to claim 1, wherein the molded body is a vascular path, an occluder, or an artificial tendon.

12. The method according to claim 1, further comprising, prior to the step of treating, mechanically pressing the entire molded body or parts of the molded body at temperatures in the range of 10° C. to 100° C. and pressures in the range of 0.01 to 1 MPa for a pressing time of 10 -200 min.

13. The method according to claim 1, wherein the bacterial cellulose is bacterial cellulose from *Gluconacetobacter xylinus*.

14. The method according to claim 1, further comprising producing the molded body of bacterial cellulose, wherein the producing comprises forming layers having different material thicknesses in a culture vessel that comprises a gas-permeable silicone layer having a variable thickness, wherein a culture solution is contacted to the gas-permeable silicon layer.

15. The method according to claim 1, further comprising producing the molded body of bacterial cellulose and cleaning the body of bacterial cellulose, wherein the cleaning comprises killing bacteria with an alkaline surfactant and a base, lysing the bacteria with microwave radiation, neutralizing the molded body, and removing bacterial particles from the molded body.

16. The method according to claim 15, wherein the surfactant concentration is 1 -10% by weight.

17. The method according to claim 15, wherein the base is selected from one or more of the group consisting of sodium hydroxide, potassium hydroxide, alkali and earth alkali carbonates, alkali and earth alkali hydrogencarbonate, ammonia and triethyl amine.

18. The method according to claim 15, wherein the alkaline surfactant is an anionic surfactant.

19. The method according to claim 15, wherein the alkaline surfactant is a nonionic surfactant.

20. The method according to claim 15, wherein the alkaline surfactant is a zwitterionic surfactant.

21. The method according to claim 15, wherein said lysing comprises incubating the body of bacterial cellulose in an enzymatic solution of at least one lytic enzyme at about 37° C. for at least 15 minutes.

22. A method for producing a storable and swellable molded body made of bacterial cellulose, wherein the method comprises steps of:
    providing a molded body of the bacterial cellulose, the bacterial cellulose in the molded body consisting of fibers of bacterial cellulose without foreign polymers;
    treating the molded body with a treatment solution comprising
        35% by weight to 75% by weight of a C1-C3 alcohol
        5% by weight to 25% by weight of water and
        20 -50 % by weight of glycerol; and
    drying the treated molded body.

23. The method according to claim 22, wherein the C1-C3 alcohol is 2-propanol.

24. A method for producing a storable and swellable molded body made of bacterial cellulose, wherein the method comprises steps of:
    providing a molded body made of the bacterial cellulose without foreign polymers;
    treating the molded body with a treatment solution comprising
        20% by weight to 50% by weight of glycerol and 50% by weight to 80% by weight of a C1-C3-alcohol/water mixture; and
    drying the treated molded body, further comprising producing the molded body of bacterial cellulose and cleaning the body of bacterial cellulose, wherein the cleaning comprises:
        a) transferring the body of bacterial cellulose into an aqueous solution of 1-10% by weight of at least one surfactant and 0.4 -4% by weight of at least one base,
        b) microwave treating the body of bacterial cellulose at a temperature of at least 80° C., but less than 100° C., for 30-60 min,
        c) washing the body of bacterial cellulose in a solution of aqueous acid in combination with application of microwaves, and rinsing with water.

* * * * *